United States Patent [19]

Franco et al.

[11] Patent Number: 4,478,824

[45] Date of Patent: Oct. 23, 1984

[54] METHOD FOR ALTERING RED BLOOD CELL FUNCTION AND SURVIVAL

[76] Inventors: Robert S. Franco, 1825 Sandcliff Dr., Cincinnati, Ohio 45230; Murray Weiner, 8915 Spooky Ridge La., Cincinnati, Ohio 45242

[21] Appl. No.: 521,078

[22] Filed: Aug. 8, 1983

[51] Int. Cl.³ .............................................. A61K 35/18
[52] U.S. Cl. ................................................... 424/101
[58] Field of Search ........................................ 424/101

[56] References Cited

PUBLICATIONS

Parsons et al.–Chem. Abst., vol. 91 (1979), p. 68355d.
Zimmermann et al.–Chem. Abst., vol. 94 (1981), p. 90235y.
Zimmermann et al.–Chem. Abst., vol. 89 (1978), p. 135851m.
Zimmermann et al.–Chem. Abst., vol. 86 (1977), p. 34,228w.

*Primary Examiner*—Sam Rosen
*Attorney, Agent, or Firm*—Frost & Jacobs

[57] ABSTRACT

Method and apparatus for creating reversible intracellular hypertonicity in red blood cells of mammals in order to introduce desired materials into the cells or achieve therapeutically desirable changes in the characteristics of intracellular hemoglobin. A packed red blood cell fraction is incubated in a solution containing a compound which readily diffuses into and out of the cells; a trans-membrane osmotic gradient is rapidly created by contacting the cells with a near-isotonic aqueous medium with or without a desired agent to be introduced, causing diffusion of water into the cells with consequent swelling thereof and permitting diffusion of said compound out of the cells; and the cells are then separated and washed to obtain a sterile fraction of substantially intact cells.

25 Claims, 3 Drawing Figures

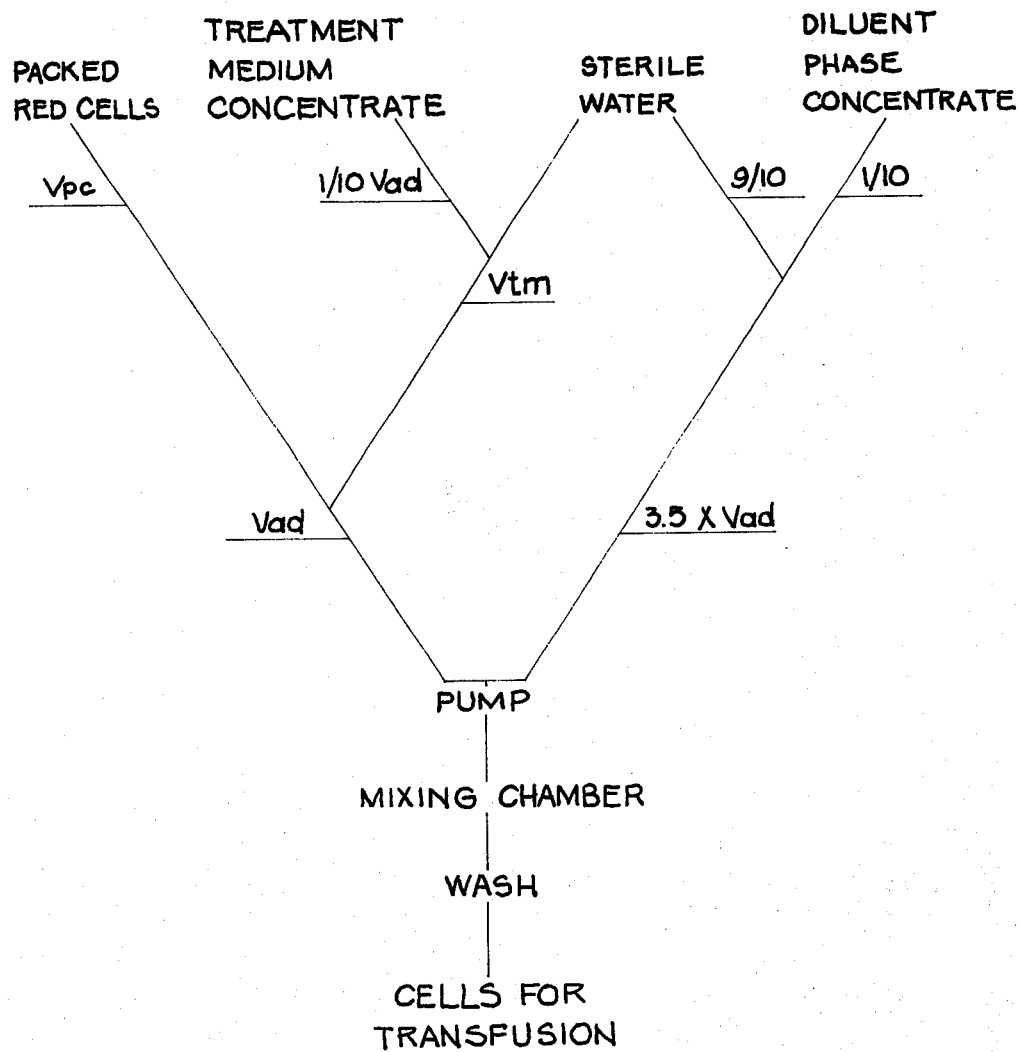

METHOD FOR ALTERING RED BLOOD CELL FUNCTION AND SURVIVAL

BACKGROUND OF THE INVENTION

This invention relates to the use of highly water soluble, uncharged, safe materials to create reversible intracellular hypertonicity as a means of incorporating desired materials into red blood cells or achieving therapeutically desirable changes in the characteristics of intracellular hemoglobin. A particular utility relates to its ability to reduce the mean corpuscular hemoglobin concentration, thereby inhibiting the precipitation or gelation of abnormal hemoglobins such as S hemoglobin and the destruction of cells by sickling.

In a specific embodiment the method of the present invention effects the introduction of materials into red blood cells by subjecting red blood cells which have been separated from whole blood to incubation with dimethyl sulfoxide or glycerol, and to a transient osmotic shock in the presence of an organic phosphate (which decreases the affinity of hemoglobin for oxygen) in a diluent solution as a result of which the cell membranes are rendered more permeable or porous, thus permitting passage of the organic phosphate into the cells. The osmotic balance is then restored and the cells resume their normal shape.

As is well known, hemoglobin (hereinafter Hb) in red blood cells (hereinafter RBC) transports oxygen from the lungs to body tissues. The normal oxygen-Hb dissociation curve (representing the reversible oxy- and deoxy-Hb equilibrium) indicates that Hb is substantially completely saturated at the oxygen partial pressure of the alveoli and substanially less than saturated at normal oxygen partial pressures in tissues which are adequate to allow aerobic metabolism.

Conditions can occur which cause a "left shift" in the oxygen-Hb dissociation curve, i.e., the Hb develops a stronger affinity for oxygen, resulting in decreased oxygen release at the normal oxygen partial pressure of tissue. For example, blood stored under blood bank conditions undergoes a left shift due to disappearance of naturally occurring 2,3 Bis phosphoglycerate (2,3 DPG), which binds reversibly to Hb and reduces its oxygen affinity.

Other compounds are known to have an even stronger effect, viz., phosphorylated inositols. Inositol hexaphosphate (hereinafter IHP) is reported to have the strongest "right shift" effect on the Hb dissociation curve. IHP is a commonly occurring plant product also known as phytic acid. However, IHP cannot penetrate the membranes of RBC, and if administered in vivo, will precipitate because of its strong affinity for calcium ions. Accordingly, incorporation of IHP intracellularly in RBC can be effected only by special techniques.

An article by G. I. Dale et al, Biochem Med 18:220–225 (1977) describes a previously known method for incorporating materials into RBC which involves rupturing RBC by osmotic swelling. This is done by suspending RBC in a hypotonic solution. Thereafter the osmotic pressure is returned to isotonic which allows the RBC membranes to reseal. All such methods suffer from the disadvantage of loss of substantial portions of the cell contents, particularly Hb, which decreases the integrity and viability of the cells reformed by resealing of membranes treated by these methods.

U.S. Pat. No. 4,192,869, issued to Nicolau and Gersonde, discloses the interaction of RBC with liposomes containing an allosteric effector, particularly IHP.

European patent application published Nov. 24, 1982 as EP No. 0065 292, in the names of Gersonde and Weiner, describes a method of freeze-preserving preparations of lipid vesicles containing allosteric effectors for eventual thawing and use.

The method of U.S. Pat. No. 4,192,869 requires the use of lipid materials (derived from sources outside the organism being treated), which may be incorporated into RBC membranes. In actual practice it has been found that the method of this patent produces inconsistent results and unpredictable failures to incorporate IHP into RBC. A number of variables, such as degree of aeration, pH control, and timing and volume of buffer washes, have been found to affect the degree of IHP incorporation, but the interdependence and possible criticality of these parameters has not been determined.

Other disclosures relating to introduction of allosteric effectors into RBC include:

M. Weiner, "Right Shifting of Hb-$O_2$ Dissociation in Viable Red Cells by Liposomal Technique" *Biol. Cell*, 47, 65–70 (1983); and R. S. Franco, M. Weiner, K. Wagner and O. J. Martelo, "Incorporation of Inositol Hexaphosphate into Red Blood Cells Mediated by Dimethyl Sulfoxide" *Life Sciences*, 32, 2763–2768 (1983).

Numerous articles are referenced in the above publications which are of background interest.

SUMMARY OF THE INVENTION

It is an object of the invention to provide a method and apparatus for introducing desired agents such as allosteric effectors of Hb into RBC without substantial loss of the contents of the cells and loss of viability thereof, which avoids the disadvantages of the above described prior art methods. The present invention has utility in providing RBC having low affinity for oxygen for respiratory investigations and research, and for treating blood which either has or has not undergone the above described left shift.

Another objective of the invention is to induce a reduction in mean corpuscular hemoglobin concentration (hereinafter MCHC) of cells such as sickle cells which survive longer when MCHC is lower. The invention thus has utility in research on and treatment of sickle cell anemia.

According to the invention there is provided a method of introducing desired agents into erythrocyte cells without substantial loss of the contents of the cells and damage to the outer membranes thereof, comprising the steps of:

separating erythrocyte cells from a supply of blood;

suspending and incubating said cells in a solution containing a compound which readily diffuses into and out of said cells, the concentration of said compound being sufficient to ensure diffusion thereof into said cells so that the contents of said cells become hypertonic;

rapidly creating a trans-membrane osmotic gradient by contacting said cells with an essentially isotonic aqueous medium in the presence of a desired agent to be introduced, whereby to cause diffusion of water into said cells with consequent swelling thereof and increase in permeability of the outer membranes of said cells;

maintaining said increse in permeability of said membranes for a period of time sufficient only to permit transport of said desired agent into said cells and diffusion of said compound out of said cells; and separating and washing said cells whereby to obtain a sterile fraction of substantially intact cells containing intracellular desired agent and substantially devoid of excess water and of other reagents.

By practicing the invention as described above with or without the addition of an agent such as an allosteric effector, cells can be produced with a uniformly slightly larger volume and slightly lower hemoglobin content per cell, resulting in a reduced MCHC which has special clinical utility as herein described.

The invention thus provides a method of reducing the mean corpuscular hemoglobin concentration of red blood cells whereby to inhibit the precipitation of abnormal hemoglobins and premature destruction thereof by sickling, comprising the steps of:

separating red blood cells from a supply of blood to obtain a suspension of packed cells;

suspending and incubating said cells in a solution containing a compound which readily diffuses into and out of said cells, the concentration of said compound being sufficient to ensure diffusion so that the contents of said cells become hypertonic;

rapidly creating a trans-membrane osmotic gradient by contacting said cells with an essentially isotonic aqueous medium whereby to cause diffusion of water into said cells with consequent swelling thereof and increase in the permeability of the outer membranes of said cells;

maintaining said increase in permeability of said membranes for a period of time sufficient only to permit diffusion of said compound and a desired volume of hemoglobin out of said cells; and separating and washing said cells whereby to obtain a sterile fraction of cells containing a reduced mean corpuscular hemoglobin concentration and substantially devoid of excess water and of said compound.

The invention further provides apparatus for introducing desired agents into erythrocyte cells comprising means for separating erythrocyte cells from a supply of blood; means for mixing the separated cells with a solution of a compound which readily diffuses into and out of said cells; first pump means communicating with said mixing means for pumping said cells in said solution at constant rate and volume; second pump means for pumping an aqueous medium containing a desired agent at constant rate and volume, said second pump means being of greater capacity than said first pump means; a chamber adapted to receive the respective output from said first and second pump means and to permit mixing of said outputs at constant ratio equal to that of said respective pump means; means to receive the mixture from said chamber; and means to separate and wash the cells.

BRIEF DESCRIPTION OF THE DRAWING

Reference is made to the accompanying drawing wherein:

FIG. 3 is a flow diagram of a continuous process embodying the invention.

DETAILED DESCRIPTION

Figure 1:
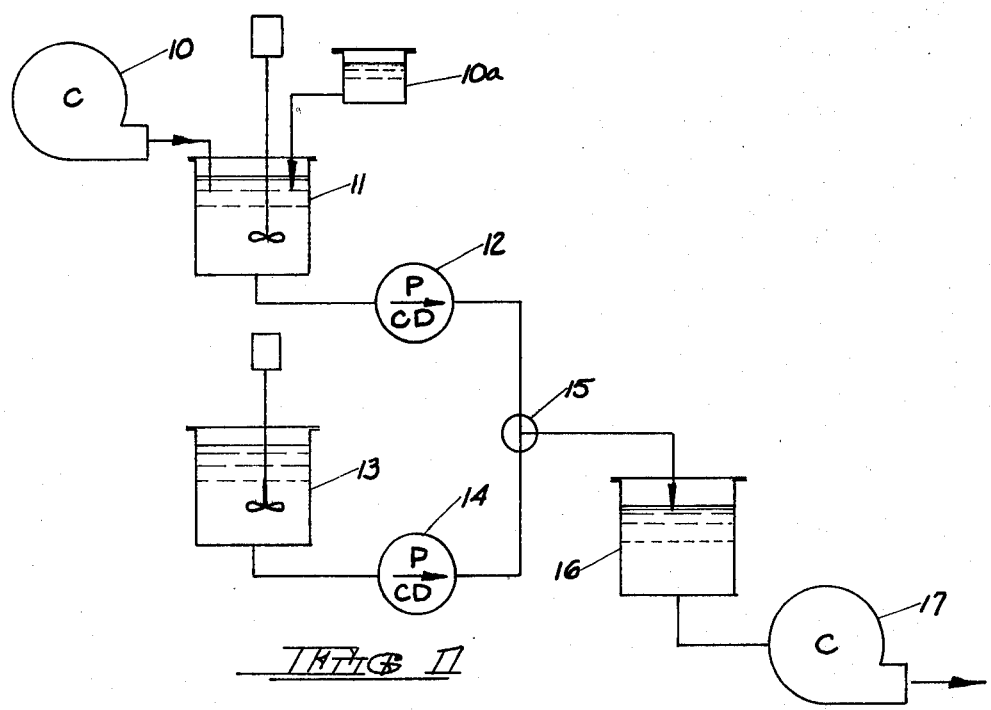
FIG. 1 is a schematic illustration of apparatus embodying the invention.

As indicated above, the method and apparatus of the invention provide incorporation of materials such as allosteric effectors into RBC by a controlled increase of RBC membrane porosity or "leakiness" so that an allosteric effector can enter and remain in the RBC without resort to exotic lipids and with limited loss of intracellular Hb. Materials used in the method of the invention are of a type which have been proven to be non-toxic and are currently used in high concentrations for the freeze preservation of structural intact blood elements. Preferred materials used in the method include dimethyl sulfoxide (hereinafter DMSO), glycerol and phosphorylated inositols, particularly inositol hexaphosphate.

DMSO and glycerol are highly water soluble and readily diffuse into and out of intact membranes of RBC. By introducing a concentration of DMSO into RBC sufficient to create hypertonicity in the cells, and then inducing a carefully controlled degree of "osmotic shock" at an appropriate temperature, relatively short exposure time, and tonicity, by contact with a volume of a near-isotonic aqueous medium containing an allosteric effector such as IHP, incorporation of the effector can be achieved rapidly, and the cells "healed" or restored to their original form before unacceptable losses of hemoglobin out of the RBC occur. It will be recognized that the method and apparatus of the present invention do not require dialysis systems of any type, and the method can be conducted at a fixed convenient temperature including ambient temperature. The method is relatively quick and simple, which is of course advantageous from the standpoint of practicality, and also provides the following desirable results:

The RBC are in a pathological porous state only for a short time.

Hb and other cell contents have little time to diffuse out of the cells, i.e. intracellular and extracellular components do not reach equilibrium by the time the desired incorporation of an allosteric effector is completed and the cell restored to its original shape.

The method can be conducted both as a continuous flow and as a batch system of treatment.

In the preferred practice of the method, RBC is separated from whole blood as by centrifuging to obtain a relatively highly packed cell volume having a concentration of about 40% to about 80% by volume. The cells are suspended in a solution containing from about 4% to about 10% by weight DMSO, and some IHP is also preferably present in the solution in a concentration ranging from about 2% to about 4% by weight.

After incubation of the suspended cells in the solution of DMSO and IHP for a period of time up to about 15 minutes, the RBC suspension is mixed rapidly with a diluting aqueous medium which contains about 2% to about 4% by weight IHP. The volume ratio of the aqueous medium to the RBC ranges from at least 1:3 to about 12:1, preferably about 2:1 to about 8:1. At the time of mixing, the diluent aqueous medium is near-isotonic, which is considerably less tonic than the RBC by reason of the prior diffusion or migration of DMSO into the cells. It will be understood that the time course of tonicity of the cells relative to the diluent aqueous medium can be controlled by the volume ratio of the medium to the cells, the concentration of DMSO in the suspension, by the tonicity contributed by the concentration of IHP in the aqueous medium, and by the temperature.

The temperature of the diluent medium is important. At about 37° C. no incorporation of IHP (and no loss of Hb) occurs at the conditions described hereinafter in Example I. At room temperature a large increase in affinity takes place with a corresponding loss of Hb from the cells. At 0° C. it was found that almost complete loss of Hb from the cells occurred. Accordingly, a temperature range of about 20° to about 30° C. for the diluent medium should be observed.

After the rapid mixing or dilution, the mixture may be incubated at room temperature for a variable period of time which is not critical. The RBC are then separated as by centrifuging and washed with appropriate solutions, after which the washed cells may be resuspended in blood plasma.

Although not wishing to be bound by theory, it is believed that the incubation with DMSO results in penetration thereof into the cells with consequent increase in osmolality. When the cell suspension containing intracellular DMSO is diluted with a near-isotonic aqueous medium containing IHP, a transient osmotic gradient is created since the DMSO leaves the cells more slowly than the water enters. This osmotic stress results in swelling of the cells and stretching of the cell membranes which permits IHP to pass into the cells. At the same time, some Hb leaves the cells, and DMSO also gradually leaves the cells. By appropriate use of a proper polymer such as polyethylene glycol, the ratio of degree of IHP incorporation and Hb loss can be favorably altered. When the DMSO has left the cells, the osmotic balance is restored, and the cells return to their original shape. It should be understood that the swelling and stretching is of relatively brief duration since the influx of water and IHP and diffusion of DMSO out of the cells apparently occur in a matter of seconds. The action can be described as analogous to a "pulsing".

It has been found that the dilution step must be performed rapidly, otherwise no incorporation of IHP into the RBC occurs. This is consistent with the hypothesis proposed above since rapid mixing is necessary to induce an osmotic gradient before DMSO diffuses out of the cells. As stated above, the dilution ratio is also important. On the other hand, it has been found that an increase in concentration of IHP in the diluent aqueous medium does not result in greater incorporation of IHP. In fact, the opposite has been observed, the percent of IHP being inversely proportional to the degree of incorporation thereof into RBC. This is again consistent with the hypothesis of a transient osmotic shock mechanism, since a higher concentration of IHP in the diluent would result in a lesser osmotic gradient across the cell membranes upon dilution.

During post-dilution incubation, the RBC appear to be relatively insensitive to the conditions under which incubation is conducted. This is also consistent with the hypothesis, since at this time incorporation of IHP has taken place, and the cell has returned to its original shape and is no longer subjected to an osmotic gradient.

Loss of Hb from the cells (hemolysis) during the treatment is of course a matter of concern. Initial tests indicated that no significant incorporation of IHP occurred unless the treatment conditions were severe enough to result in at least 20% hemolysis. However, it was found that the addition of a relatively small amount of an appropriate polymer in the diluent aqueous medium resulted in reduction of the loss of Hb from the RBC to an acceptable level. Up to about 5% by weight polyethylene glycol having a molecular weight of about 500 to about 8000 has been found to be effective for this purpose, with the higher molecular weight preferred at about 1% concentration. While not essential in the present method, since a reduced corpuscular Hb concentration might be desired for some purposes, (such as sickle cell anemia), the use of a polyethylene glycol additive in the diluent aqueous medium is greatly preferred where the purpose is to facilitate aerobic metabolism in body tissue.

Referring to FIG. 1 of the drawing, centrifugal means for separating RBC from whole human blood is indicated generally at 10. A vessel for mixing the separated cells with a solution of DMSO and IHP supplied from vessel 10a is shown at 11. Communicating therewith is a first pump indicated at 12 for pumping the cells suspended in the solution at a constant rate and volume. An aqueous medium containing IHP is supplied from a mixing vessel 13 to a second pump indicated at 14 which also provides pumping at constant rate and volume. The second pump 14 is of greater capacity than the first pump and delivers a volume of diluent at least $\frac{1}{3}$ the output of the first pump and preferably from 2 to 8 times the volume. However the pressure of both pump outputs should be the same.

The outputs from pumps 12 and 14 are delivered to a chamber indicated at 15, which need be of no particular dimension as long as adequate mixing is assured, and can in fact be a three-way mixing valve. It is at this point that the rapid dilution, osmotic shock and resultant swelling of the RBC occur, during which time the IHP diffuses into the cells.

The mixture is then conducted to a receiver indicated at 16 in which further incubation is conducted. This may be maintained at atmospheric pressure. Thereafter the RBC fraction is separated and washed by conventional means indicated at 17.

Illustrative but non-limiting examples of the method of the invention are as follows:

EXAMPLE I

Blood was drawn (from a human subject) using citrate vacutainers (Monoject # HRI 9981-340478) and centrifuged for 5 minutes at 1000 g. The plasma was saved for later use, the buffy coat was discarded, and the RBC were washed once with Buffer A (20.92 g bistris pH 7.4 and 4.97 g Na Cl per liter) and centrifuged under the same conditions. One-half ml of the packed RBC was added to 2 ml of cold IHP solution (3.34% IHP Sigma # P-5756, pH adjusted to 7.2 with H Cl), and the suspension was placed on ice.

In a separate container 0.391 ml of DMSO was added to 2 ml of the same IHP solution and placed on ice. The RBC suspension and the DMSO-IHP solution were mixed together and placed on ice. The DMSO concentration at this point was 8% by weight. After two minutes the mixture was removed from the ice, and 55 ml of the same IHP solution at 25° C. were added rapidly, the dilution ratio being 11.2:1 by volume. The mixture was incubated for 15 minutes at room temperature. The RBC were then separated by centrifuging (5 mins. 1000 g) and washed twice with a hypertonic buffer (20.92 g bistris pH 7.4 and 6.97 g Na Cl per liter), twice with the above-described Buffer A and once with autologous plasma. The washed RBC were resuspended in autologous plasma for determination of the Hb-oxygen equilibrium curve, as discussed hereinafter.

Figure 2:
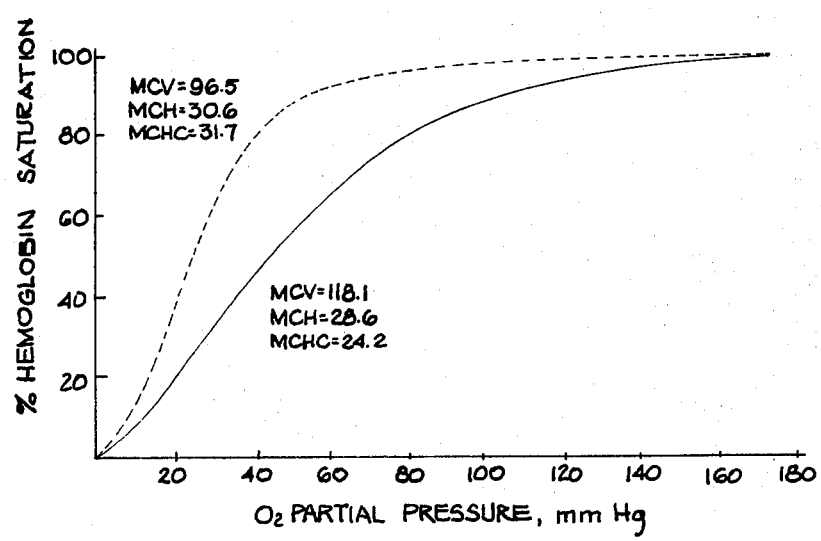
FIG. 2 is a graphic representation of hemoglobin-oxygen equilibrium curves.

Referring to FIG. 2, Hb-oxygen equilibrium curves were developed using a HemOScan oxygen dissociation analyzer (American Instrument Co.) in accordance with the manufacturer's directions. The normal range for P50 in these tests was 25.6±0.8 mm Hg (1 sd), n=8.

Standard red cell indices were measured for cells treated in accordance with Example I and for control cells treated by the same method except for omission of DMSO. Indices were measured in homologous plasma by an electronic counter (Model S plus, Coulter Electronics).

Total RBC hemoglobin present before and after the processing of Example I was measured as A540 after conversion to cyanomethemoglobin.

FIG. 2 illustrates the right shift of the dissociation curve resulting from the method of the invention as compared to the control cells. The solid line represents RBC treated in accordance with the method of the invention, while the dashed line represents RBC treated in the same manner without DMSO. The RBC treated according to Example I had a P50 of 47±10 mm Hg (1 sd, n=9) and a significant increase in size. Some loss of Hb from the cells occurred (43±14% [1 sd, n=9]), but the surviving cells had only a slightly decreased mean corpuscular hemoglobin as shown in FIG. 2.

Example II

The method of Example I was followed with the following changes:

The packed cell volume in the suspension before dilution was increased to 50% by volume.

The concentration of DMSO in the suspension before dilution was decreased to 7% by weight.

The volume ratio of diluent IHP solution was reduced to 5:1.

1% polyethylene glycol (M.W. 3500) was added to the diluent aqueous medium.

The procedure of Example II represents a preferred embodiment of the method of the invention when practiced as a batch-type operation. The following advantages are obtained:

Hemolysis is decreased for the same degree of IHP incorporation.

Cells have a more uniform appearance after processing, i.e. restoration to the original biconcave disc shape.

A greater volume of RBC is treated per volume of suspension.

Since the volume of extracellular fluid per volume of RBC suspension is reduced, the effective diluent ratio (diluent:extracellular fluid) is increased and less total diluent is required to produce the same osmotic gradient.

EXAMPLE III

Utilizing the apparatus of FIG. 1 described above, a continuous treatment of any desired volume of blood is conducted in accordance with the method of the invention. The RBC concentration of the suspension is preferably maintained between about 40% and 60% by volume. The DMSO concentration is maintained between about 4% and 10% by weight, preferably between 5% and 7%. This influences the degree of IHP incorporation. The diluent: RBC ratio is maintained between about 1:3 and about 12:1 by volume, preferably about 2:1 to 8:1.

While the above tests were conducted with human RBC, the same method has been successful in introducing IHP into rabbit and pig RBC.

EXAMPLE IV

Referring to FIG. 3, there is shown incorporation of IHP with a continuous flow method using economical reagent concentrates. Materials and software as well as a procedure for utilizing these materials in the practice of the invention, as illustrated in FIG. 3, are as follows:

1. Materials

A. Concentrate of a solution for cell treatment (treatment medium concentrate):

A standard bottle with 50 ml of a sterile aqueous solution containing 27.5 ml of DMSO 55% and 16.7 gms IHP adjusted to pH 7.2.

B. Concentrate of a solution of diluent (diluent phase concentrate):

A standard bottle with 200 ml of a sterile aqueous solution containing 20 g PEG (10%) and 61 gms IHP (30.5%) adjusted to pH 7.2.

C. Sterile distilled water for injection.

2. Hardware

A. A cell washing system adapted from standard bank methods, IBM programmed centrifuge (ex for frozen cells), Hemonetic "Cell Saver" type apparatus, or first phase of apheresis type apparatus (Parker).

B. A peristaltic pump such as Masterflex System (Curtin-Matheson) capable of acting simultaneously on two tubes of different diameter or two separate independent pumping systems such as the Fisher catalog No. 13-875-105.

3. Disposable Software

A. Bags to make solution dilutions.
B. "T" tube to serve as mixing chamber.
C. tubing of specified diameter to go from cell suspension bag and diluent solution bag through pump to mixing chamber, and from mixing chamber to bag for cell washing.

4. Procedure

A. Preparation of red cell treatment suspension:
 1. Prepare packed (washed) red cells by a standard method.
 2. Weigh to determine volume (Vpc).
 3. Determine hematocrit (H).

5. Calculate (a) Volume of cells = Vpc × H/100
(b) Adjusted volume (Vad) to obtain a hematocrit of 50%: Vad = 2 × Vpc × H/100 = Vpc × H/50
(c) Volume of treatment medium (Vtm) needed to bring hematocrit to 50. Vtm = (2 × Vpc × H/100) − Vpc = Vpc(H/50 − 1)

6. Prepare required volume of treatment medium (Vtm) by adding (a) An amount of treatment medium concentrate (Vtmc) which is 1/10 of the calculated adjusted volume (Vad) of the cell suspension to
(b) Distilled water to bring to Vtm, i.e. Vtm minus Vtmc 7. Add treatment medium prepared per the above to the packed red cells.

8. Prepare diluent (a) Calculate volume needed, e.g., 3.5×Vad (b) Add 1/10 that volume of diluent concentrate to 9/10 that volume of sterile water.

9. Processing red cells

1. Attach appropriate tubes from suspended cell and diluent preparations to mixing chamber via peristaltic pump and connect mixing chamber outflow to cell washing bag or into a "Cell Saver" type apparatus.
2. Open clamps and turn on pump to a flow rate of about 25 ml/min red cell suspension and 86/ml/min diluent.
3. Wash processed cells twice with two volumes of saline.
4. Deliver packed cells for transfusion in usual manner.

We claim:

1. A method of introducing desired agents into erythrocyte cells without substantial loss of the contents of the cells and damage to the outer membranes thereof, comprising the steps of:
   separating erythrocyte cells from a supply of blood;
   suspending and incubating said cells in a solution containing a compound which readily diffuses into and out of said cells, the concentration of said compound being sufficient to ensure diffusion thereof into said cells so that the contents of said cells become hypertonic;
   rapidly creating a trans-membrane osmotic gradient by contacting said cells with an essentially isotonic aqueous medium in the presence of a desired agent to be introduced, whereby to cause diffusion of water into said cells with consequent swelling thereof and increase in permeability of the outer membranes of said cells;
   maintaining said increase in permeability of said membranes for a period of time sufficient only to permit transport of said desired agent into said cells and diffusion of said compound out of said cells; and
   separating and washing said cells whereby to obtain a sterile fraction of substantially intact cells containing intracellular desired agent and substantially devoid of excess water and of other reagents.

2. The method of claim 1, wherein said compound which readily diffuses into and out of said cell is dimethyl sulfoxide, glycerol, or mixtures thereof.

3. The method of claim 1, wherein said desired agent is an allosteric effector of hemoglobin.

4. The method of claim 3, wherein said allosteric effector is a phosphorylated inositol.

5. The method of claim 4, wherein said phosphorylated inositol is inositol hexaphosphate.

6. The method of claim 1, wherein said erythrocyte cells are red blood cells of a mammal.

7. The method of claim 1, wherein the temperature of said aqueous medium is from about 20° to about 30° C.

8. The method of claim 1, wherein said aqueous medium contains up to about 5% polyethylene glycol having a molecular weight of about 500 to 8,000, whereby to inhibit loss of hemoglobin from said cells.

9. The method of claim 1, wherein said solution containing said compound which readily diffuses into and out of said cells further contains a desired agent to be introduced into red cells.

10. The method of claim 9, wherein said desired agent is an allosteric effector of hemoglobin.

11. The method of claim 1, wherein the volume ratio of said essentially isotonic aqueous medium to said cells is at least 1:3.

12. The method of claim 2, wherein the concentration of said dimethyl sulfoxide, glycerol, or mixtures thereof ranges from about 5% to 10%.

13. A method of decreasing the affinity of hemoglobin in mammalian red blood cells for oxygen without substantial loss of viability of said cells, comprising the steps of:
    separating red blood cells from a supply of blood to obtain a suspension of packed cells;
    suspending and incubating said cells in a solution containing about 4% to about 10% by weight dimethyl sulfoxide, glycerol, or mixtures thereof whereby to cause diffusion of said dimethyl sulfoxide, glycerol, or mixtures thereof into said cells;
    rapidly contacting the suspension with an aqueous medium in the presence of a phosphorylated inositol at a volume ratio of said medium to said cells ranging from at least 1:3 to about 8:1, the medium being at a temperature of about 20° to about 30° C., whereby to effect diffusion of water into said cells with consequent swelling and increase in permeability thereof;
    maintaining said increase in permeability for a period of time sufficient only to permit transport of said phosphorylated inositol into said cells and diffusion of said dimethyl sulfoxide, glycerol, or mixtures thereof out of said cells; and
    separating and washing said cells thereby obtaining a sterile fraction of substantially intact cells containing intracellular phosphorylated inositol and substantially devoid of excess water and of dimethyl sulfoxide, glycerol, or mixtures thereof.

14. The method of claim 13, wherein said steps are conducted at ambient temperature.

15. The method of claim 13, wherein said aqueous medium contains about 1% by weight polyethylene glycol having a molecular weight of about 500 to 8000, whereby to inhibit loss of hemoglobin from said cells.

16. The method of claim 13, wherein said solution contains at least one phosphorylated inositol.

17. The method of claim 13, wherein said aqueous medium is near isotonic with respect to said cells.

18. The method of claim 13, wherein said phosphorylated inositol is inositol hexaphosphate.

19. The method of claim 18, wherein the concentration of said inositol hexaphosphate in said aqueous medium is from about 2% to 4%.

20. A method of reducing the mean corpusclar hemoglobin concentration of red blood cells whereby to inhibit the precipitation of abnormal hemoglobins and premature destruction thereof by sickling, comprising the steps of:
    separating red blood cells from a supply of blood to obtain a suspension of packed cells;
    suspending and incubating said cells in a solution containing a compound which readily diffuses into and out of said cells, the concentration of said compound being sufficient to ensure diffusion so that the contents of said cells become hypertonic;
    rapidly creating a trans-membrane osmotic gradient by contacting said cells with an essentially isotonic aqueous medium whereby to cause diffusion of water into said cells with consequent swelling thereof and increase in the permeability of the outer membranes of said cells;

maintaining said increase in permeability of said membranes for a period of time sufficient only to permit diffusion of said compound and a desired volume of hemoglobin out of said cells; and separating and washing said cells whereby to obtain a sterile fraction of cells containing a reduced mean corpuscular hemoglobin concentration and substantially devoid of excess water and of said compound.

21. The method of claim 20, wherein said compound which readily diffuses into and out of said cells is dimethyl sulfoxide, glycerol, or mixtures thereof.

22. The method of claim 20, wherein the volume ratio of said aqueous medium to said cells is at least 1:3.

23. The method of claim 20, wherein at least one of said solution and said aqueous medium further contains a desired agent to be introduced into said cells.

24. The method claimed in claim 23, wherein said desired agent is an allosteric effector of hemoglobin.

25. The method claimed in claim 24, wherein said allosteric effector is a phosphorylated inositol.

* * * * *